United States Patent
Shields et al.

(10) Patent No.: US 10,892,041 B2
(45) Date of Patent: Jan. 12, 2021

(54) METHOD AND APPARATUS FOR DETERMINING COMPLEXITY OF A CLINICAL TRIAL

(71) Applicant: Medidata Solutions, Inc., New York, NY (US)

(72) Inventors: Lori Shields, Glenside, PA (US); Joshua Hartman, Conshohocken, PA (US)

(73) Assignee: Medidata Solutions, Inc., New York, NY (US)

( * ) Notice: Subject to any disclaimer, the term of this patent is extended or adjusted under 35 U.S.C. 154(b) by 1786 days.

(21) Appl. No.: 14/136,300

(22) Filed: Dec. 20, 2013

(65) Prior Publication Data
US 2015/0178244 A1    Jun. 25, 2015

(51) Int. Cl.
G06F 17/10 (2006.01)
G16H 10/20 (2018.01)
G16H 50/30 (2018.01)

(52) U.S. Cl.
CPC ............. G16H 10/20 (2018.01); G16H 50/30 (2018.01)

(58) Field of Classification Search
CPC .... G06F 19/363; G06F 19/3431; G06F 19/30; G06F 9/44; G06Q 50/24; G06Q 50/22
See application file for complete search history.

(56) References Cited

U.S. PATENT DOCUMENTS

| 8,606,594 B2 | 12/2013 | Stern et al. | |
| 2004/0093240 A1* | 5/2004 | Shah | G06F 19/363 |
| | | | 705/2 |
| 2004/0236601 A1 | 11/2004 | Summers et al. | |
| 2004/0249664 A1 | 12/2004 | Broverman et al. | |
| 2006/0179418 A1 | 8/2006 | Boyd | |
| 2007/0156459 A1 | 7/2007 | McMahon et al. | |
| 2008/0114616 A1 | 5/2008 | Ferguson | |
| 2008/0172251 A1* | 7/2008 | Reichert | G06Q 50/22 |
| | | | 705/2 |
| 2010/0262436 A1 | 10/2010 | Chen et al. | |

(Continued)

FOREIGN PATENT DOCUMENTS

| KR | 1020050085171 A | 8/2005 |
| WO | 2012/151402 A1 | 11/2012 |

OTHER PUBLICATIONS

Cattie, Frank, "Understanding Protocol Complexity Produces More Accurate Investigator Site Budgets," PharmaVoice, vol. 12, No. 10, Nov./Dec. 2012.

(Continued)

*Primary Examiner* — Mohamed Charioui
*Assistant Examiner* — Jeremy A Delozier
(74) *Attorney, Agent, or Firm* — Steptoe & Johnson LLP; Robert Greenfeld

(57) ABSTRACT

A method for determining net complexity of a clinical trial includes determining procedures to be performed during the clinical trial, determining which of the procedures may be routinely performed on clinical trial subjects suffering from the disease that the drug under test is designed to treat, determining the net procedures to be performed for the clinical trial itself, and calculating a complexity score for the net procedures. An apparatus for determining net complexity of a clinical trial is also described and claimed.

14 Claims, 2 Drawing Sheets

(56) References Cited

U.S. PATENT DOCUMENTS

2010/0324931 A1 12/2010 Mancini et al.
2011/0153358 A1* 6/2011 Campo ................ G06F 19/363
705/2

OTHER PUBLICATIONS

Glass, Harold, "Standard of Care in Clinical Study Budgeting," Applied Clinical Trials Online, Jul. 1, 2010 (available at http://www.appliedclinicaltrialsonline.com/standard-care-clinical-study-budgeting, last accessed Jul. 18, 2016).
Kuzma, Dawn, "Clinical Trial Budget Development," Aug. 2012.
"Medidata Solutions Introduces New Web-Based Version of Clinical Trial Budgeting Application with Complexity Metric," Jun. 14, 2010 (available at https://www.mdsol.com/en/newsroom/press-release/medidata-solutions-introduces-new-web-based-version-clinical-trial-budgeting-application, last accessed Jul. 18, 2016).
pharmavoice.com, "A New Era of Collaboration: Knowledge Sharing—Demystifying Routine Care Coverage in Trial Budgeting," Podcast Transcript with Jessica Dolti and Kelly Willenberg, Dec. 27, 2012 (available at http://www.pharmavoice.com/content/industryevents/transcriptMedidata_Dolfi.html as of Oct. 9, 2014).
The International Search Report and the Written Opinion of the International Searching Authority, PCT/US2014/070590, dated Mar. 31, 2015.
The International Search Report and Written Opinion of the International Searching Authority, PCT/US2014/070604, dated Mar. 26, 2015.

\* cited by examiner

METHOD AND APPARATUS FOR DETERMINING COMPLEXITY OF A CLINICAL TRIAL

CROSS-REFERENCE TO OTHER APPLICATIONS

This application includes subject matter that overlaps with a pending patent application assigned to the assignee of this application, Medidata Solutions, Inc. That application is entitled, "Method and Apparatus for Generating a Clinical Trial Budget," has U.S. application Ser. No. 14/136,034, and is being filed on the same date as this application. The entire disclosure of that patent application is incorporated herein by reference.

BACKGROUND

Clinical studies or trials to test drugs or devices are very data intensive and can be very expensive. These clinical trials often involve patients who already suffer from the disease for which the drug under study is being tested. Thus, these patients are already being seen by physicians and are likely undergoing procedures, such as medical histories, blood draws, blood pressure or other vitals readings, and x-rays, that would also be performed during the study.

Figure 1:
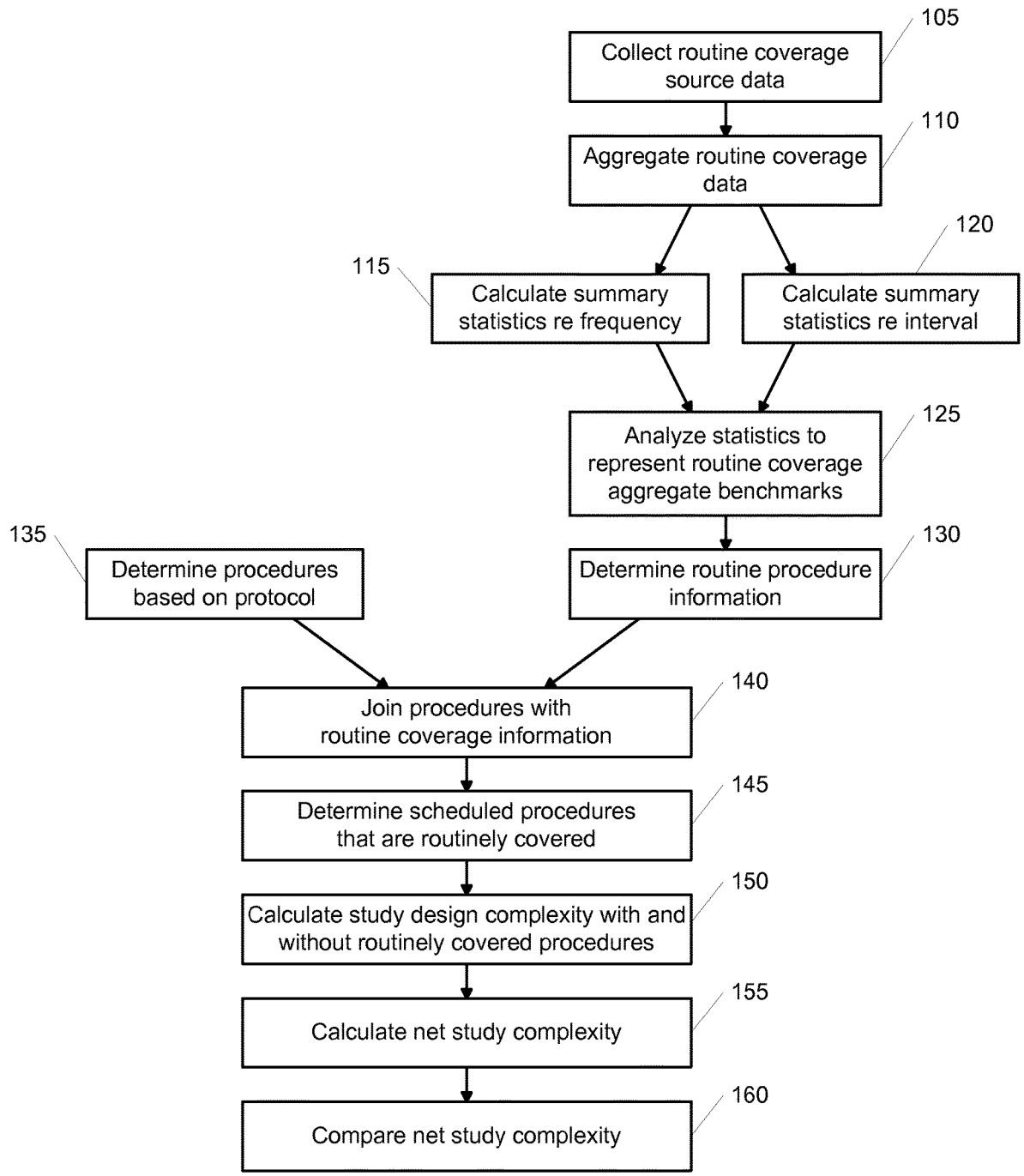
FIG. 1 is a flowchart illustrating how complexity of a clinical trial may be determined, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The parties involved in a clinical drug trial may like to know beforehand how complex the trial will be. A sponsor, such as a drug manufacturer, of a clinical drug trial or a contract research organization (CRO) that performs a clinical trial for a sponsor may like to compare the complexity of different possible trials and choose the least complex design that will accomplish the sponsor's goals. (Hereinafter, the word "sponsor" means sponsor or CRO or any other entity or person who plans or runs a clinical trial.) A site that participates in a clinical trial, such as a doctor's office, a section of a hospital, or a clinic, may be approached by a number of sponsors to perform trials and the site may want to compare the complexity of the different offers in order to choose the least complex. A site that has participated in clinical trials in the past may also want to compare the complexity of a proposed trial with that of a previously completed trial in order to gauge how easy or difficult it may be to recruit patients for the proposed trial.

One way of determining complexity includes using the concept of a "protocol complexity metric" or "site work effort" (SWE). See, e.g., "Understanding Protocol Complexity Produces More Accurate Investigator Site Budgets," PharmaVoice, vol. 12, no. 10 (November/December 2012). This metric measures the effort required by site staff to implement the procedures in a clinical trial protocol. As discussed in U.S. Pat. Pub. No. 2011/0153358, commonly assigned to Medidata Solutions, Inc., applicant of this application, SWE may be determined by summing up the "procedure work effort" (PWE) of each procedure, where the PWE may be calculated by multiplying a "work effort unit" (WEU) value by the number of occurrences of each unique procedure. The entire disclosure of U.S. Pat. Pub. No. 2011/0153358 is incorporated herein by reference. In that reference, a work effort unit may be based on one or more of procedure type, cost, time, and phase.

However, because certain procedures that may be performed during a clinical trial would be routinely performed anyway for a patient who is suffering from the disease that is being treated by the drug under trial, the inventors of the present invention have recognized that "net complexity" may be determined by examining those clinical trial procedures that are not routinely performed on a patient. This net complexity may provide a more accurate measure of complexity so that a site, subject, or sponsor may evaluate the prudence of a participating in a particular clinical trial.

Reference is now made to FIG. 1, which is a flowchart illustrating one way to determine net study complexity for a clinical trial. In operation 105, source data may be collected to determine "routine coverage." Routine coverage includes the clinical procedures that may routinely be performed on a patient who is suffering from a disease that a drug under trial is intended to treat. This source data may come from any source, but examples of such sources are medical claims data, from sponsors of previous clinical trials, from public databases, insurance provider guidelines, specialty disease forums, and data vendors that aggregate electronic medical record (EMR) and electronic health record (EHR) information. The data may include the procedure performed; the procedure code (if available) (one class of codes is called "CPT Codes," which stands for "current procedural terminology," and are maintained by the American Medical Association); the diagnosis or indication, which may be denoted by an ICD-9 or ICD-10 indication code; the occurrence of the disease the patient has (e.g., 1st, 2nd, 3rd, etc.), if not already included in the ICD-9 or ICD-10 code; the location of the procedure, e.g., by 3- or 5-digit ZIP code or by city, state, and/or country; the date the procedure was performed; and whether the procedure was routinely covered. Also available may be patient identification information to assist in determining how often the procedure is covered for a patient (e.g., three times) and within what interval it may be covered for that patient (e.g., per year).

In operation 110, the routine coverage data may be aggregated into defined groups, including procedure groups, diagnosis groups, and geographical groups. Aggregation may show a typical behavior grouped by a set of relevant dimensions, and may allow for larger datasets. Aggregation may take into account, for example, the disease or diseases suffered by recipients of the procedures, the stage of the disease(s) suffered by recipients of the procedures, the severity of the disease(s) suffered by recipients of the procedures, the locations of the sites where the procedures are performed (because different locations may involve different definitions of "routine"), etc. A procedure group may be defined as a group of medical procedures that share a common method of implementation. For example, an electrocardiogram (ECG) may be performed using 6 leads or 12 leads, but the primary information supplied by either methodology is the same, thus grouping those procedures together allows for a larger dataset. Similarly, a diagnosis group may be created from similar standardized indication codes, e.g., Type II Diabetes may be presented under codes 250.0, 250.01, 250.02, all of which are slightly different variations of the disease, but with very minor differences in the treatment. Examples of geographical groups may be a specific state within the United States that groups together multiple sites and multiple states that are grouped into a region.

The system may then calculate summary statistics based on the aggregated data. These statistics may include mean, median, standard deviation, mode, and various percentile information, e.g., first quartile, third quartile, etc. In operation 115, the summary statistics may describe the typical frequency of performance of a procedure in a diagnosis group, and in operation 120, the summary statistics may describe the typical interval between performances of a procedure for a diagnosis group. Next, in operation 125, the descriptive statistics may be analyzed to represent routine coverage aggregate benchmarks. In operation 130, routine procedure information may be determined, including associating procedure codes (such as CPT codes) with frequency of routine coverage information.

In operation 135, after a study protocol is designed by a sponsor, the sponsor or site principal investigator may determine the medical or clinical procedures (or activities) to be performed based on the study protocol. Such procedures may include x-rays, CT scans, blood draws, reading of vital signs, office consultations—likely any procedure for which there is a medical procedure or CPT code. Procedures without a CPT code, such as filling out questionnaires, study assessments, and other clinical study activities, may also be included. This operation may also include associating the coded procedure with its frequency and work effort unit (WEU) value.

In operation 140, the schedule of procedures (or activities) may be joined with the routine coverage information. This may be done by filtering the benchmarks from operation 125 based on the schedule of procedures determined in the study design. In operation 145, the scheduled procedures that may be routinely covered are determined, as well as the net procedures that are performed due to the clinical trial itself. In operation 150, the complexity of the study design may be calculated with and without the routinely covered procedures. Such determination may include using WEU values, site work effort (SWE), or other measures of complexity, including those disclosed in U.S. Pat. Pub. No. 2011/0153358 and "Understanding Protocol Complexity Produces More Accurate Investigator Site Budgets" (referenced above). In operation 155, a user, such as a sponsor, a principal investigator, or a subject, may calculate net study complexity by comparing the complexity of the proposed clinical trial with the complexity of the covered procedures. In operation 160, a user may then compare the net complexity of the proposed clinical trial with the net complexity of other proposed clinical trials or past clinical trials.

Figure 2:
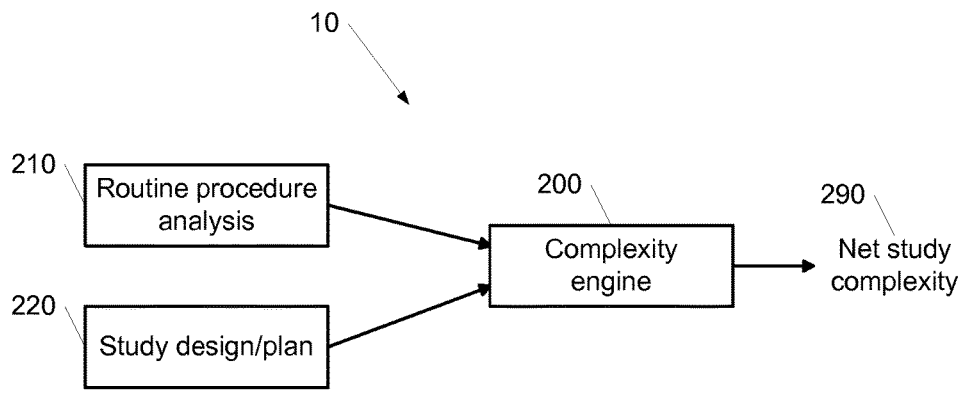
FIG. 2 is a block diagram of a system for determining complexity of a clinical trial, according to an embodiment of the present invention.

Reference is now made to FIG. 2, which is a block diagram of a complexity determination system 10 according to an embodiment of the present invention. Broadly speaking, in FIG. 2, complexity engine 200 may take as inputs routine procedure analysis 210 and study design/plan 220, and may output net study complexity 290, which may be in the form of a complexity factor or score or some other measure. Routine procedure analysis 210 may determine the routine procedures as described above in operations 105-130. Study design/plan 220 may include the medical or clinical procedures to be performed based on a study protocol, as described above in operation 135. Complexity engine 200 may determine net study complexity 290 by first joining the scheduled procedures with the routine coverage information as in operation 140, then determining the scheduled procedures that may be routinely covered as in operation 145, and then determining the complexity of the procedures that are performed due to the clinical trial itself, as in operations 150-155.

The blocks shown in FIG. 2 are examples of modules that may comprise complexity determination system 10, and do not limit the blocks or modules that may be part of or connected to or associated with complexity determination system 10. For example, complexity engine 200 may perform routine procedure analysis 210, or routine procedure analysis block 210 may perform analyses other than just routine procedure analysis. The blocks in FIG. 2 may generally be implemented in software or hardware or a combination of the two, and may include a processor, a memory, and software instructions executed by the processor.

Complexity determination system 10 may be implemented on a standalone computer or on a network, for example, over the Internet as a cloud-based service or hosted service, which may be accessed through a standard web service application programming interface (API).

Figure 3:
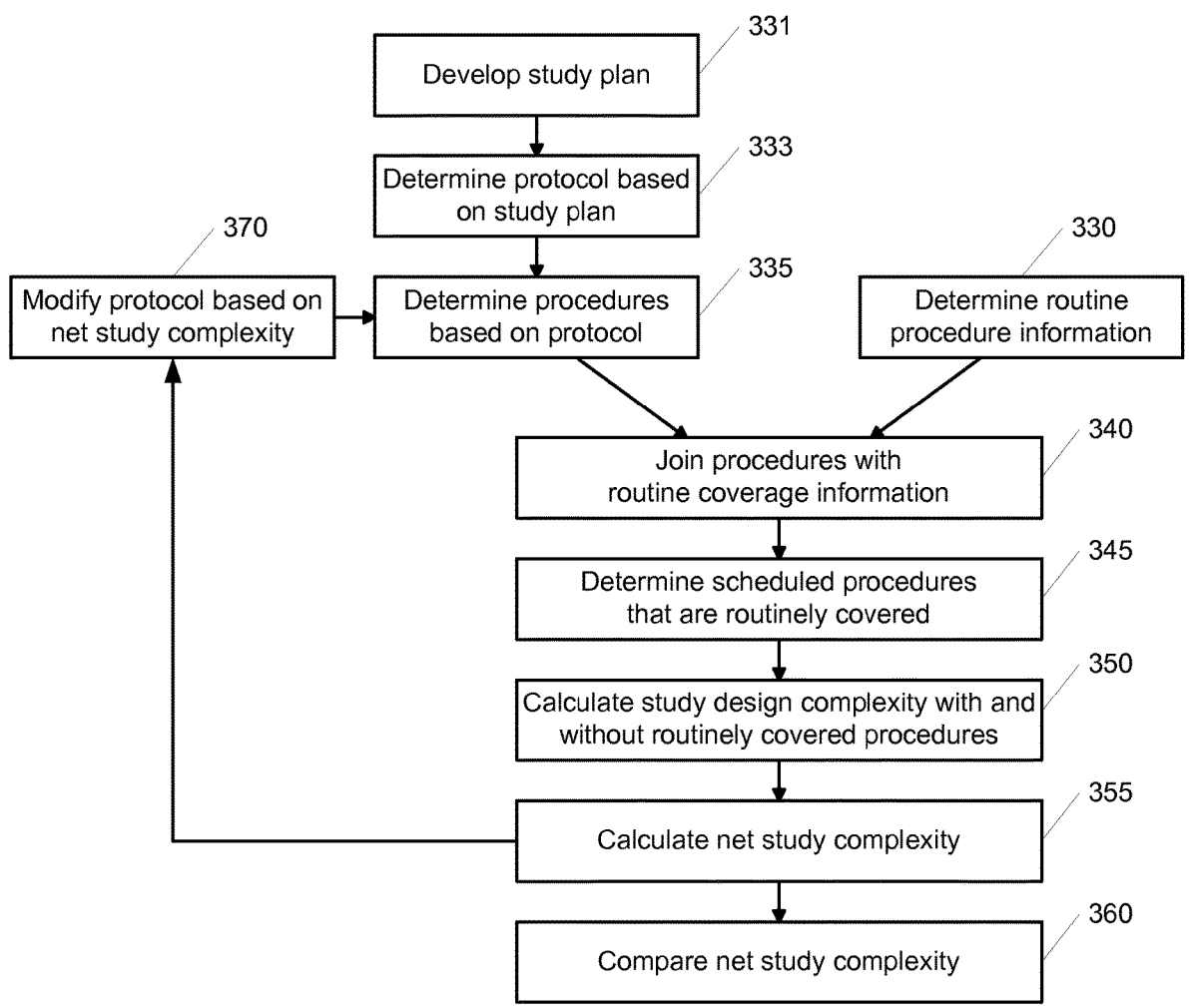
FIG. 3 is another flowchart illustrating how complexity of a clinical trial may be determined, according to another embodiment of the present invention.

Reference is now made to FIG. 3, which is a flowchart illustrating another embodiment of the present invention, showing a way in which net study complexity of a clinical trial may be used in developing a clinical study design. In operation 331, the sponsor (or study designer) may develop a study plan for the clinical trial or study. Such a plan may be an outline of the study design which may be customized to fit the final protocol design. In operation 333, the sponsor may then determine a protocol based on the study plan. Such a protocol may include a synopsis, objectives, schedule of activities, statistical plan, and outcome measures. Operation 330 may encompass prior operations, such as operations 105-125, and operations 335-360 may function essentially the same as operations 135-160, with the sponsor, principal investigator, or system determining the medical or clinical procedures (or activities) to be performed based on the study protocol, joining the scheduled procedures with the routine coverage information, determining the scheduled procedures that may be routinely covered, calculating the complexity of the study design with and without the routinely covered procedures, calculating the net study complexity, and comparing the net complexity of the proposed clinical trial with the net complexity of other proposed clinical trials or past clinical trials.

When the net study complexity in operation 355 is calculated, a feedback loop may be introduced into the flowchart of FIG. 3, as shown in operation 370. In this operation, the sponsor, site investigator, or system may modify the protocol based on the net study complexity. This may be done in order to minimize complexity of the study. For example, the study design may originally call for a procedure to be performed four times, but the routine procedure analysis may show that the procedure may be performed twice for a patient during the study as part of that patient's normal disease treatment plan. In that case, the designer or system may modify the protocol to call for the procedure to be performed only two times, in order to minimize the net complexity of the study design.

The modification in operation 370 may also be performed to possibly increase the net complexity of the study, perhaps because the study designer or sponsor wants to test out different complexity scenarios or may offer to sites a number of study plans from which to choose.

Besides the operations shown in FIGS. 1 and 3, other operations or series of operations may be contemplated to determine net complexity of a clinical trial. Moreover, the actual order of the operations in the flow diagrams is not intended to be limiting, and the operations may be performed in any practical order. For example, operation 370 may involve modifying the study plan, which, in turn may modify the protocol, in which case the output of operation 370 may be input to operation 333 rather than 335. In other embodiments, there may be other feedback processes within individual operations, such that the study plan or protocol is designed with some knowledge of the routine procedures performed for patients suffering from the disease, which may reduce the need for an explicit feedback loop in operation 370. In another embodiment, instead of having the feedback loop go from operation 355, it may go from operation 360, or there may be a joint feedback from operations 355 and 360 to operation 370.

The present invention may used to help sponsors, sites, and subjects evaluate the net complexity of a clinical trial, net of the procedures that the patient would already be subject to based on the disease the patient suffers. It is understood, however, that embodiments of the invention can be used in other fields involving clinical study feasibility, patient selection, site identification, and patient tolerance for a study design.

One benefit of the present invention is that a sponsor may more accurately understand the routine procedures for a patient suffering from a particular disease so that it can design a clinical study that may minimize the complexity of the additional procedures used for the clinical trial only. Another benefit is that the principal investigator or subject may be able to compare the complexity of a proposed clinical trial against that of prior clinical trials in order to assess the additional burdens on the site or the patient for participating in the study. A further benefit is that a site or sponsor may be better equipped to negotiate execution of a clinical trial protocol, and they may work with each other to reduce the complexity of the proposed clinical trial.

The present invention differs from other systems that may analyze complexity of a clinical trial in that those systems may analyze the total complexity of the trial, rather than the net complexity. This should provide for a more precise estimate of the added complexity of clinical trial procedures over and above what the subjects may already encounter in their normal care for treatment of the disease from which they suffer.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof, A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method for a site to determine whether to participate in a clinical trial, comprising:
   collecting source data for a plurality of clinical procedures;
   aggregating the source data to account for specific medical conditions;
   calculating, based on a statistical analysis of the aggregated source data, statistics regarding the typical frequency and interval of the performance of each procedure for specific medical conditions;
   determining a first plurality of procedures to be performed during a first clinical trial, the first plurality being a first subset of the plurality of clinical procedures for a specific medical condition;
   calculating the net complexity for the first plurality of procedures;
   determining a second plurality of procedures to be performed during a second clinical trial, the second plurality being a second subset of the plurality of clinical procedures for the specific medical condition;
   calculating the net complexity for the second plurality of procedures;
   comparing the net complexity for the first plurality of procedures to the net complexity for the second plurality of procedures; and
   selecting the clinical trial whose plurality of procedures has the lesser net complexity,
   wherein calculating the net complexity for a plurality of procedures comprises:
   calculating a complexity score for the plurality of procedures;
   determining, based on the typical frequency and interval of each procedure to be performed for a specific medical condition, which of the plurality of procedures may be routinely performed on clinical trial subjects suffering from the specific medical condition;

calculating a complexity score for the routinely performed procedures; and subtracting the complexity score for the routinely performed procedures from the complexity score for the plurality of procedures.

2. The method of claim 1, wherein the complexity score comprises work effort units, procedure work effort, and/or site work effort.

3. The method of claim 1, wherein the source data comes from one or more public databases.

4. The method of claim 1, wherein the source data comes from one or more sponsors of clinical trials.

5. The method of claim 1, wherein determining which of the procedures may be routinely performed on clinical trial subjects suffering from the specific medical condition comprises analyzing procedure data based on the specific medical condition, progression of the specific medical condition, severity of the specific medical condition, and location of patient.

6. The method of claim 1, wherein aggregating the source data comprises aggregating the data into procedure groups, diagnosis groups, and geographical groups.

7. The method of claim 1, wherein calculating a complexity score for a plurality of procedures comprises summing up the complexity scores of individual procedures within the set.

8. An apparatus for a site to determine whether to participate in a clinical trial, comprising:
 a routine procedure analysis module configured to:
  collect source data for a plurality of clinical procedures;
  aggregate the source data to account for specific medical conditions;
  calculate, based on a statistical analysis of the aggregated source data, statistics regarding the typical frequency and interval of the performance of each procedure for specific medical conditions;
 a study/design plan module configured to:
  determine a first plurality of procedures to be performed during a first clinical trial, the first plurality being a first subset of the plurality of clinical procedures for a specific medical condition;
  determine a second plurality of procedures to be performed during a second clinical trial, the second plurality being a second subset of the plurality of clinical procedures for the specific medical condition; and
 a complexity engine configured to:
  calculate the net complexity for the first plurality of procedures;
  calculate the net complexity for the second plurality of procedures;
  compare the net complexity for the first plurality of procedures to the net complexity for the second plurality of procedures; and
  select the clinical trial whose plurality of procedures has the lesser net complexity,
 wherein calculating the net complexity for a plurality of procedures comprises:
  calculating a complexity score for the plurality of procedures;
  determining, based on the typical frequency and interval of each procedure to be performed for a specific medical condition, which of the plurality of procedures may be routinely performed on clinical trial subjects suffering from the specific medical condition;
  calculating a complexity score for the routinely performed procedures; and
  subtracting the complexity score for the routinely performed procedures from the complexity score for the plurality of procedures.

9. The apparatus of claim 8, wherein the complexity score comprises work effort units, procedure work effort, and/or site work effort.

10. The apparatus of claim 8, wherein the source data comes from one or more public databases.

11. The apparatus of claim 8, wherein the source data comes from one or more sponsors of clinical trials.

12. The apparatus of claim 8, wherein determining which of the procedures may be routinely performed on clinical trial subjects suffering from the specific medical condition comprises analyzing procedure data based on the specific medical condition, progression of the specific medical condition, severity of the specific medical condition, and location of patient.

13. The apparatus of claim 8, wherein aggregating the source data comprises aggregating the data into procedure groups, diagnosis groups, and geographical groups.

14. The apparatus of claim 8, wherein calculating a complexity score for a plurality of procedures comprises summing up the complexity scores of individual procedures within the set.

* * * * *

UNITED STATES PATENT AND TRADEMARK OFFICE
CERTIFICATE OF CORRECTION

PATENT NO. : 10,892,041 B2
APPLICATION NO. : 14/136300
DATED : January 12, 2021
INVENTOR(S) : Shields et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1866 days.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*